United States Patent
Jung et al.

(10) Patent No.: US 9,301,819 B2
(45) Date of Patent: Apr. 5, 2016

(54) IMPRESSION MIXING TIP

(71) Applicant: DXM CO., LTD., Goyang (KR)

(72) Inventors: Du Rok Jung, Goyang (KR);
Kyoungsoo Shin, Goyang (KR)

(73) Assignee: DXM CO., LTD., Goyang, Gyeonggi-do (KR)

( * ) Notice: Subject to any disclaimer, the term of this patent is extended or adjusted under 35 U.S.C. 154(b) by 0 days.

(21) Appl. No.: 14/542,113

(22) Filed: Nov. 14, 2014

(65) Prior Publication Data

US 2015/0136806 A1    May 21, 2015

Related U.S. Application Data

(63) Continuation of application No. PCT/KR2013/008047, filed on Sep. 6, 2013.

(30) Foreign Application Priority Data

Sep. 5, 2013  (KR) ......................... 10-2013-0106649

(51) Int. Cl.
*B67D 7/78*   (2010.01)
*A61C 9/00*   (2006.01)
(Continued)

(52) U.S. Cl.
CPC .............. *A61C 9/0026* (2013.01); *B01F 7/0025* (2013.01); *B01F 13/0023* (2013.01); *B05C 17/00503* (2013.01); *B01F 2215/0039* (2013.01)

(58) Field of Classification Search
CPC ............ A61C 9/0025; B05C 17/00503; B01F 7/0025; B01F 13/0023; B01F 2215/0039
USPC .............. 222/145.5, 145.6; 366/162.1, 162.3, 366/181.4
See application file for complete search history.

(56) References Cited

U.S. PATENT DOCUMENTS

| | | | | |
|---|---|---|---|---|
| 4,771,919 A | * | 9/1988 | Ernst .................... | B65D 81/325 222/134 |
| 5,249,862 A | * | 10/1993 | Herold ................... | A61C 5/064 222/137 |

(Continued)

FOREIGN PATENT DOCUMENTS

WO    WO-2012116863 A1 *   9/2012

*Primary Examiner* — Paul R Durand
*Assistant Examiner* — Randall Gruby
(74) *Attorney, Agent, or Firm* — Mintz Levin Cohn Ferris Glovsky and Popeo, P.C.; Kongsik Kim

(57) ABSTRACT

A mixing tip for a dispenser according to the present invention includes a lower casing connected to the dispenser and to which a silicone base material and a curing agent are supplied, an upper casing coupled to the lower casing and including a discharge pipe through which an impression material having a desired mixing ratio of the silicone base material and the curing agent is discharged to the outside, and a mixer disposed between the lower casing and the upper casing to mix the silicone base material with the curing agent, wherein the mixer includes a mixing plate disposed between the lower casing and the upper casing and having a predetermined surface area, a shaft-fitting pipe extending downward from the mixing plate and fitted over a drive shaft of the dispenser to be rotated therewith, and a path control rib extending downward from an outer peripheral edge of the mixing plate to control flow paths of the silicone base material and the curing agent, wherein the lower casing includes a body including an upper casing-fitting ring formed at an outer peripheral edge thereof and coupled to the upper casing and an inner fitting ring spaced apart from the upper casing-fitting ring by a predetermined interval and extending from the body, a base material supply pipe extending downward from a bottom surface of the body to receive the silicone base material and to discharge the silicone base material into a mixing space defined between the path control rib and the mixing plate, and a curing agent supply pipe spaced from the base material supply pipe to receive the curing agent and to discharge the curing agent into a space defined between the path control rib and the inner fitting ring.

9 Claims, 7 Drawing Sheets

(51) Int. Cl.
*B05C 17/005* (2006.01)
*B01F 7/00* (2006.01)
*B01F 13/00* (2006.01)

(56) References Cited

U.S. PATENT DOCUMENTS

| | | | | |
|---|---|---|---|---|
| 5,609,271 A | * | 3/1997 | Keller | B05C 17/00506 222/145.6 |
| 6,135,631 A | * | 10/2000 | Keller | 366/339 |
| 6,244,740 B1 | * | 6/2001 | Wagner et al. | 366/181.5 |
| 6,394,643 B1 | * | 5/2002 | Bublewitz et al. | 366/172.1 |
| 6,398,761 B1 | * | 6/2002 | Bills et al. | 604/191 |
| 6,443,612 B1 | * | 9/2002 | Keller | 366/307 |
| 6,523,992 B1 | * | 2/2003 | Bublewitz | A61C 5/064 222/145.6 |
| 6,837,612 B2 | * | 1/2005 | Bublewitz et al. | 366/172.1 |
| 7,320,541 B2 | * | 1/2008 | Wagner | B01F 7/00141 222/145.6 |
| D617,001 S | * | 6/2010 | Lee | D24/220 |
| 7,771,110 B2 | * | 8/2010 | Wang | B01F 5/0615 366/155.1 |
| 7,866,509 B2 | * | 1/2011 | Ziesel | B67D 1/0044 222/145.1 |
| 8,100,295 B2 | * | 1/2012 | Keller | B05C 17/00506 222/137 |
| 8,322,909 B2 | * | 12/2012 | Gramann | B01F 7/00291 366/172.2 |
| 8,365,958 B2 | * | 2/2013 | Ho | B01F 5/0615 222/137 |
| D693,940 S | * | 11/2013 | Walter | D24/220 |
| 8,876,364 B2 | * | 11/2014 | Gartmann et al. | 366/172.1 |
| 2001/0005338 A1 | * | 6/2001 | Muhlbauer | A61C 5/064 366/307 |
| 2003/0137898 A1 | * | 7/2003 | Wagner | B01F 7/00125 366/172.1 |
| 2004/0085854 A1 | * | 5/2004 | Pauser | B01F 15/0201 366/172.1 |
| 2004/0257909 A1 | * | 12/2004 | Pieroni | 366/172.1 |
| 2005/0205606 A1 | * | 9/2005 | Nehren | B05C 17/00553 222/145.5 |
| 2005/0230422 A1 | * | 10/2005 | Muller | B05C 17/00553 222/145.6 |
| 2005/0232073 A1 | * | 10/2005 | Wagner et al. | 366/172.1 |
| 2008/0029542 A1 | * | 2/2008 | Keller | B05C 17/00553 222/145.5 |
| 2008/0264809 A1 | * | 10/2008 | Knispel | A61C 5/064 206/219 |
| 2009/0207685 A1 | * | 8/2009 | Busin et al. | 366/15 |
| 2009/0296516 A1 | * | 12/2009 | Keller | 366/160.5 |
| 2010/0012210 A1 | * | 1/2010 | Miyano | A61C 5/064 137/896 |
| 2010/0200614 A1 | * | 8/2010 | Von Rotz et al. | 222/145.5 |
| 2010/0208544 A1 | * | 8/2010 | Wintergerste et al. | 366/134 |
| 2010/0252574 A1 | * | 10/2010 | Busin | A61C 5/064 222/137 |
| 2011/0114672 A2 | * | 5/2011 | Boudy | A23G 3/0021 222/145.3 |
| 2012/0279988 A1 | * | 11/2012 | Hiemer | A61C 9/0026 222/82 |
| 2013/0329517 A1 | * | 12/2013 | Linne et al. | 366/290 |

* cited by examiner

IMPRESSION MIXING TIP

CROSS-REFERENCE TO RELATED APPLICATIONS

This is a continuation of International Application No. PCT/KR2013/008047 filed on Sep. 6, 2013, which claims priority to Korean Application No 10-2013-0106649 filed on Sep. 5, 2013. The applications are incorporated herein by reference.

TECHNICAL FIELD

The present invention relates to a mixing tip for a dispenser, and more particularly to a mixing tip for a dispenser which has an improved construction for mixing materials for preparing a dental impression.

BACKGROUND ART

In dentistry, a dental impression material that is prepared by mixing a liquid-phase silicone base material with a curing agent is used in order to obtain a dental impression. The impression material is usually received in an impression material cartridge assembly before use thereof. The impression material cartridge assembly includes impression material cartridges which accommodate the silicone base material and the curing agent, respectively, and a mixing tip coupled to the impression material cartridges to mix the materials and to discharge the resulting mixture.

Referring to Korean Patent Registered No. 10-0914836, there is disclosed a conventional coupling structure between impression material cartridges and a mixing tip.

FIG. 1 is a cross-sectional view showing a construction of a conventional mixing tip 10. As illustrated in the drawing, the conventional mixing tip 10 includes a lower casing 11, an upper casing 15 coupled to the lower casing 11, and a mixer 17 rotatably disposed in both the casings. A silicone base material A is introduced through a first flow path 12 formed in the lower casing 11 while a curing agent B is introduced through a second flow path 13 formed in the lower casing 11. Both the materials are mixed with each other at a predetermined mixing ratio by means of a mixer 17, and the resulting impression material C is discharged to the outside.

The conventional mixing tip 10 is constructed such that the silicone base material A and the curing agent B are mixed in a predetermined mixing ratio and then discharged. Since the first flow path 12 and the second flow path 13 have different diameters, upon initial application of the same discharge pressure to the flow paths, the silicone base material A is first discharged for a certain period of time from the first flow path 12 having a larger diameter and the curing agent B is subsequently discharged from the second flow path 13.

Consequently, only the silicone base material A is discharged without discharge of an impression material having a desired mixing ratio for an initial certain period of time after application of an actuation signal. Therefore, the discharge of the impression material involves a cumbersome work in that a user has to discard the initially discharged silicone mixture and to wait for discharge of the impression material mixed at the desired mixing ratio.

SUMMARY

Therefore, the present invention has been made in view of the above problems, and it is an object of the present invention to provide a mixing tip for a dispenser capable of discharging an impression material having a desired mixing ratio even from the time the impression material is first discharged.

The above and other objects and various advantages of the invention will appear more fully to those skilled in the art from a consideration of the following description of embodiments of the present invention.

The above object can be accomplished by the provision of a mixing tip for a dispenser. The mixing tip for a dispenser according to the present invention includes; a lower casing connected to the dispenser and to which a silicone base material and a curing agent are supplied, an upper casing coupled to the lower casing and including a discharge pipe through which an impression material having a desired mixing ratio of the silicone base material and the curing agent is discharged to the outside, and a mixer disposed between the lower casing and the upper casing to mix the silicone base material with the curing agent, wherein the mixer includes, a mixing plate disposed between the lower casing and the upper casing and having a predetermined surface area, a shaft-fitting pipe extending downward from the mixing plate and fitted over a drive shaft of the dispenser to be rotated therewith, and a path control rib extending downward from an outer peripheral edge of the mixing plate to control flow paths of the silicone base material and the curing agent, wherein the lower casing includes, a body including an upper casing-fitting ring formed at an outer peripheral edge thereof and coupled to the upper casing and an inner fitting ring spaced apart from the upper casing-fitting ring by a predetermined interval and extending from the body, a base material supply pipe extending downward from a bottom surface of the body to receive the silicone base material and to discharge the silicone base material into a mixing space defined between the path control rib and the mixing plate, and a curing agent supply pipe spaced apart from the base material supply pipe to receive the curing agent and to discharge the curing agent into a space defined between the path control rib and the inner fitting ring.

In an aspect, the base material supply pipe may be provided at an inner surface thereof with an inclined guide surface for guiding the curing agent introduced from the dispenser toward the inner fitting ring.

In another aspect, the inner fitting ring may be provided at an inner surface thereof with a curing agent guide groove having a predetermined depth, which is connected to an upper end of the curing agent supply pipe to guide the curing agent toward the outside of the path control rib.

Furthermore, the above object can be accomplished by the provision of a mixing tip for a dispenser including, a lower casing connected to the dispenser and to which a silicone base material and a curing agent are supplied, an upper casing coupled to the lower casing and including a discharge pipe through which an impression material having a desired mixing ratio of the silicone base material and the curing agent is discharged to the outside, and a mixer disposed between the lower casing and the upper casing to mix the silicone base material with the curing agent, wherein the mixer includes, a mixing plate disposed between the lower casing and the upper casing and having a predetermined surface area, and a shaft-fitting pipe extending downward from the mixing plate and fitted over a drive shaft of the dispenser to be rotated therewith, wherein the lower casing includes, a body including an upper casing-fitting ring formed at an outer peripheral edge thereof and coupled to the upper casing and an inner fitting ring spaced apart from the upper casing-fitting ring by a predetermined interval and extending from the body, a base material supply pipe extending downward from a bottom surface of the body to receive the silicone base material and to discharge the silicone base material into a mixing space under the mixing plate, and a curing agent supply pipe spaced from the base material supply pipe to receive the curing agent and to discharge the curing agent along the inner fitting ring.

The mixing tip for a dispenser according to the present invention can eliminate the difference in supply time between a silicone base material and a curing agent which are discharged in the early phase of actuation, by adjusting supply paths of the silicone base material and the curing agent.

Consequently, it is possible to make even a portion of an impression material that is initially discharged have a desired mixing ratio, and thus it is possible to eliminate the conventional problems that an initially discharged portion of an impression material has to be discarded.

DETAILED DESCRIPTION

Figure 1:
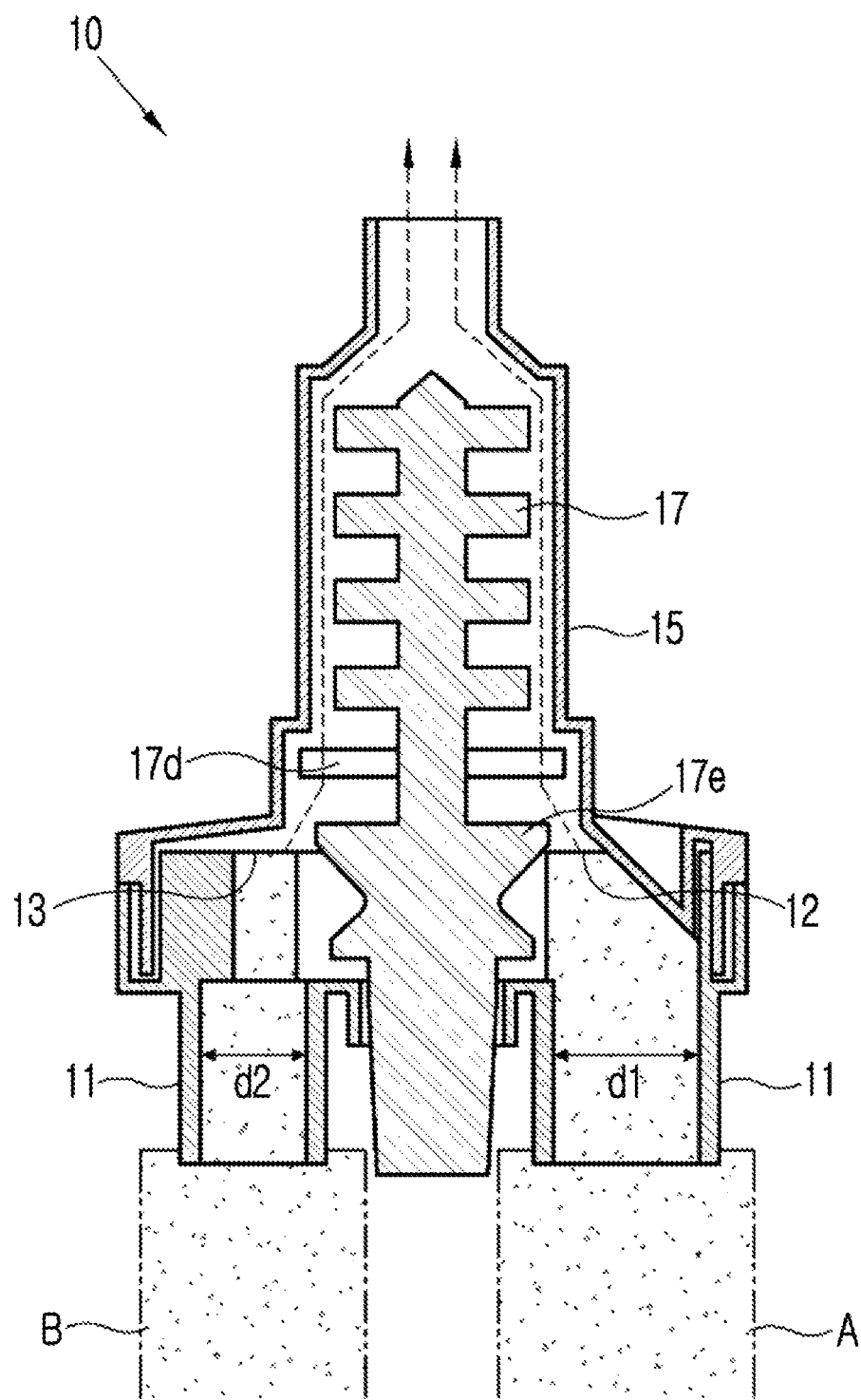
FIG. 1 is a schematic view showing a cross-section of a conventional mixing tip.

Preferred embodiments of the present invention will be described with reference to the accompanying drawings for the full understanding. The embodiments of the present invention may be changed to a variety of embodiments and the scope and spirit of the present invention should not be construed as being limited to the embodiment described hereinbelow. The embodiments of the present invention are provided for allowing those skilled in the art to more clearly comprehend the present invention. Therefore, it should be understood that the shape and size of the elements shown in the drawings may be exaggerated to provide an easily understood description of the structure of the present invention. It is to be noted that the same reference numerals will be used throughout the drawings and the description to refer to the same or like parts. In the following description of the present invention, detailed descriptions of known functions and components incorporated herein will be omitted when it may make the subject matter of the present invention unclear.

Figure 2:
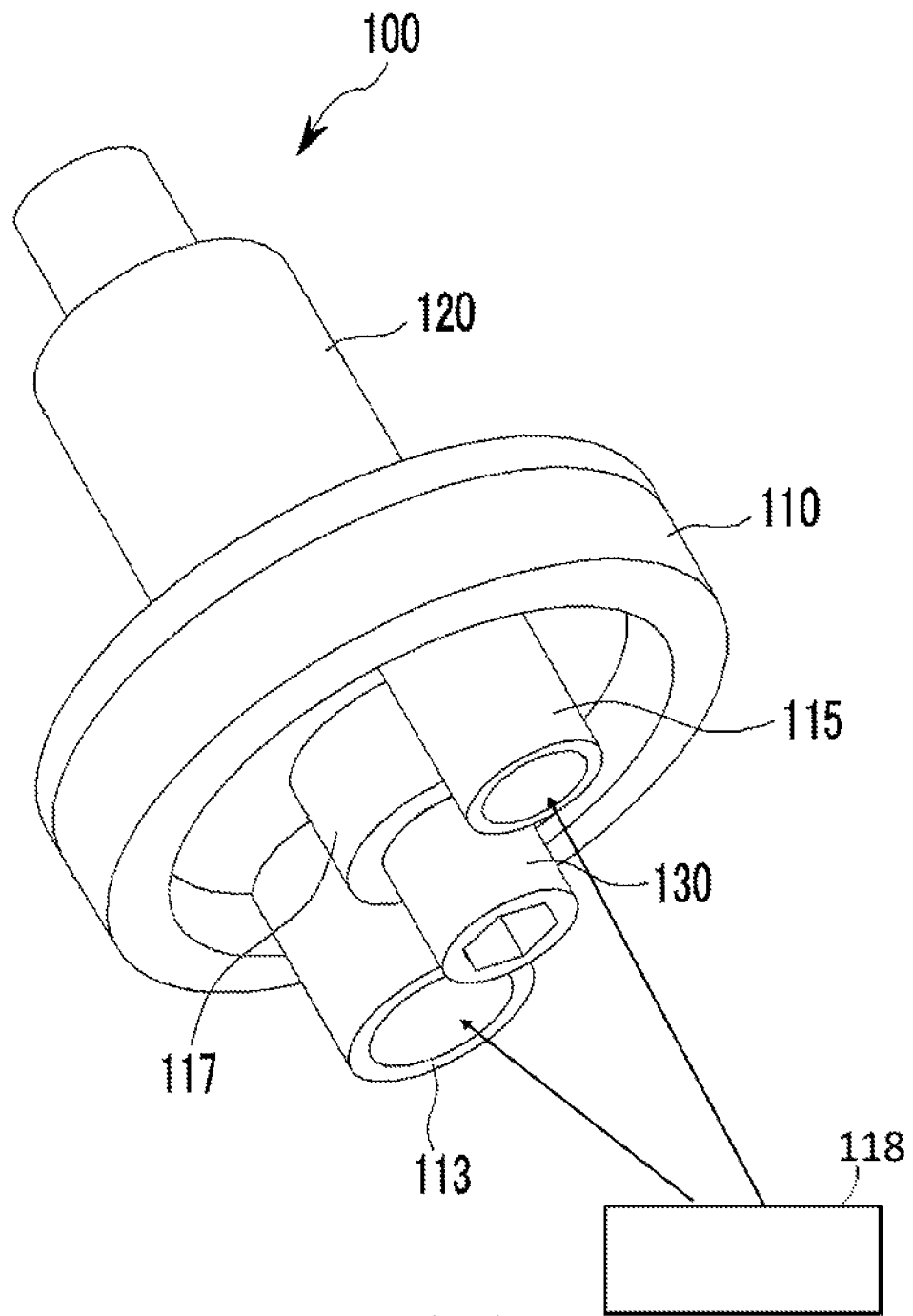
FIG. 2 is a perspective view showing an external construction of a mixing tip according to the present invention.
Figure 3:
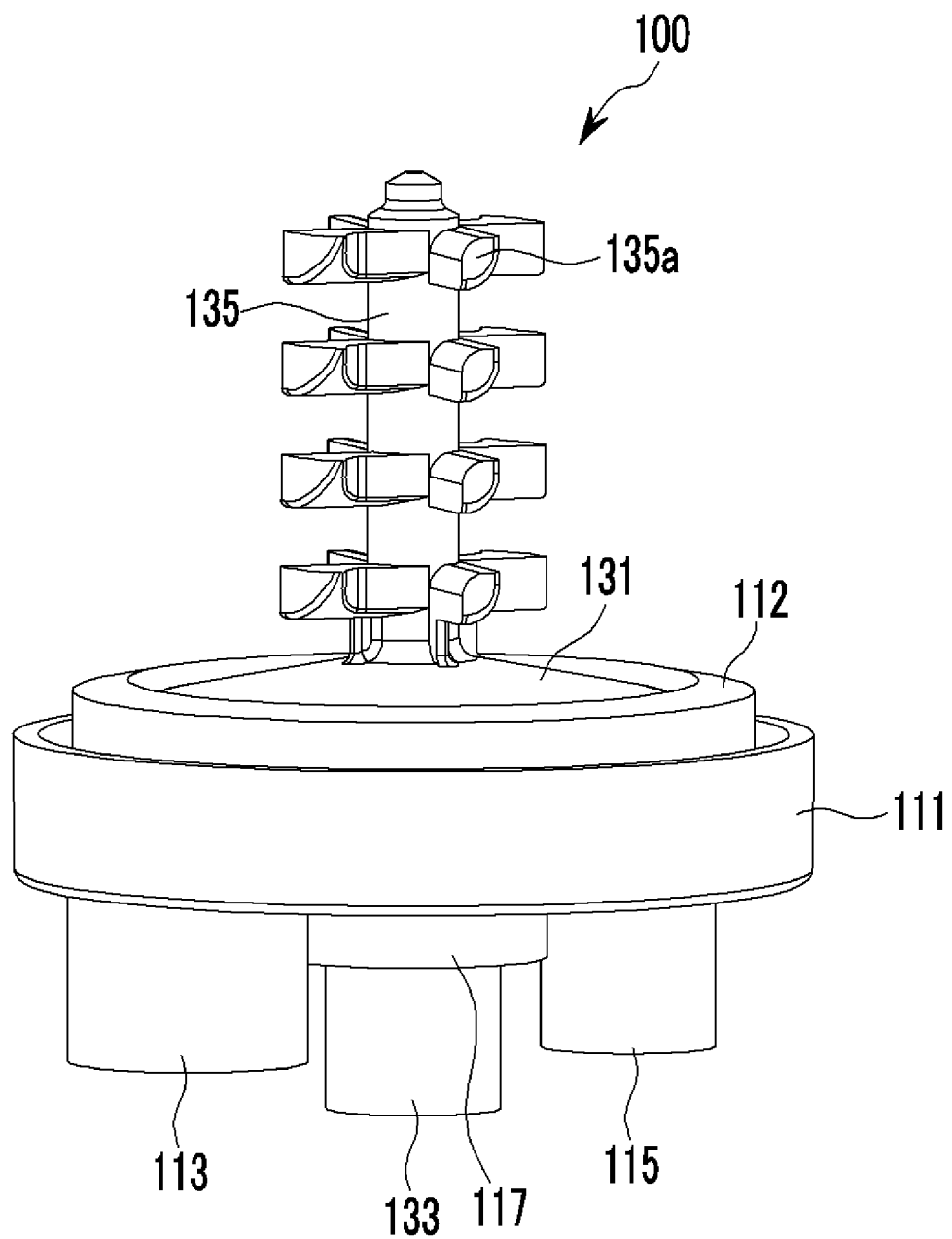
FIG. 3 is a perspective view showing an internal construction of the mixing tip according to the present invention.
Figure 4:
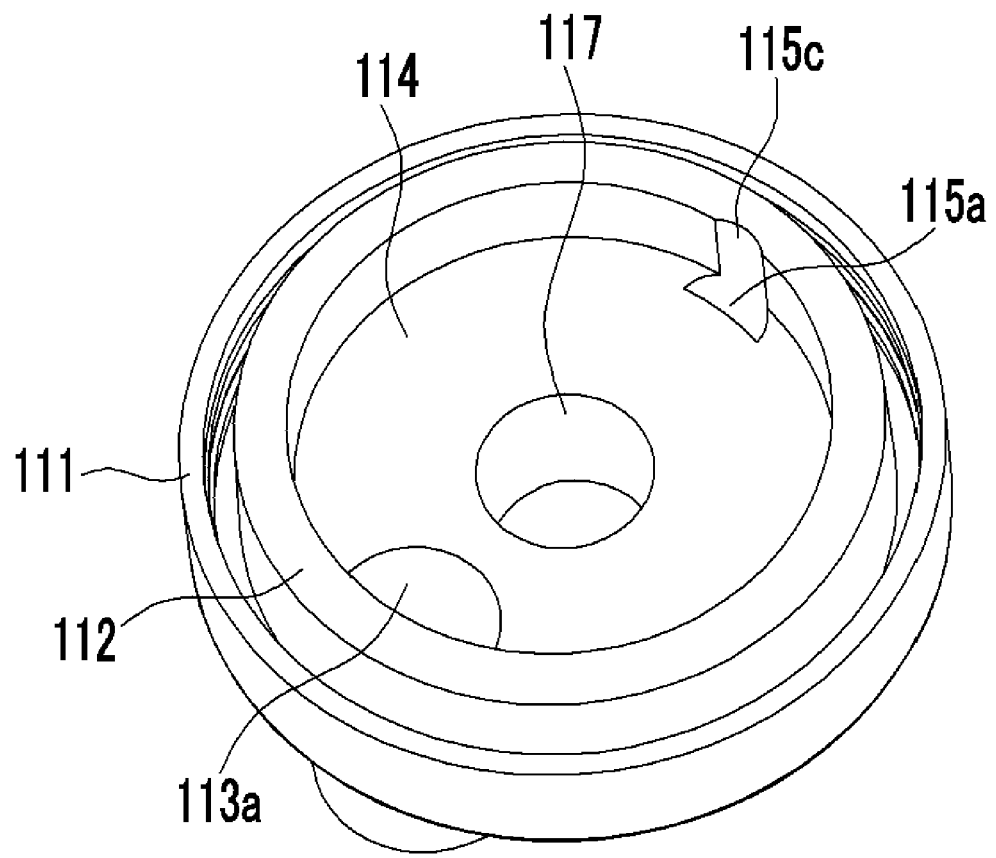
FIG. 4 is a perspective view showing a lower casing of the mixing tip according to the present invention.
Figure 5:
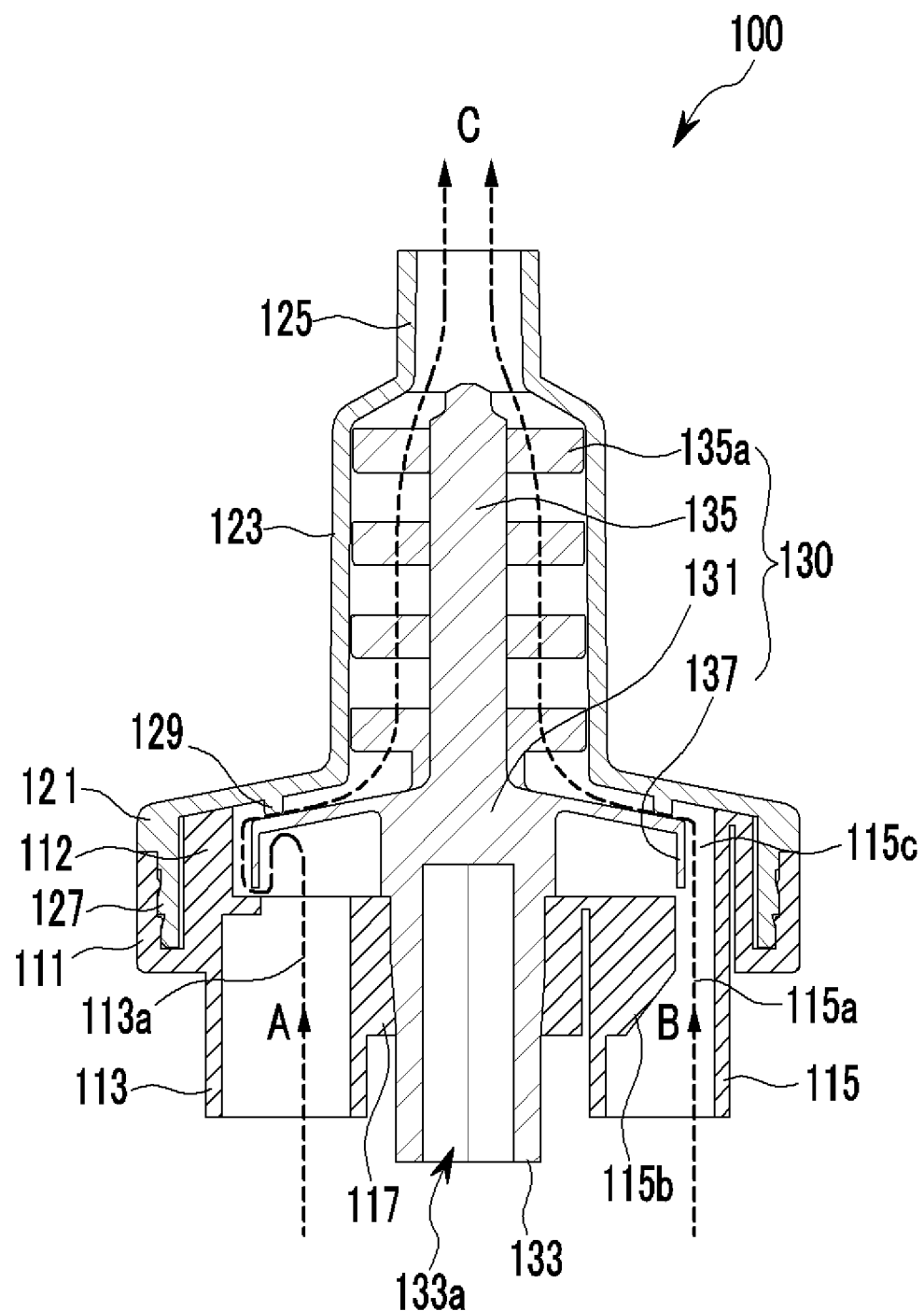
FIG. 5 is a cross-sectional view showing a cross-section of the mixing tip according to the present invention.

FIG. 2 is a perspective view illustrating an external construction of a mixing tip 100 according to the present invention. FIG. 3 is a cross-sectional view illustrating an internal construction of the mixing tip 100. FIG. 4 is a perspective view illustrating a lower casing 110 of the mixing tip 100. FIG. 5 is a cross-sectional view illustrating a cross-sectional construction of the mixing tip 100.

The mixing tip 100 according to the present invention is coupled to an impression material cartridge mounted on a dispenser (not shown) adapted to automatically dispense an impression material. The dispenser 118 schematically shown in FIG. 2 is configured to supply a silicone base material A and a curing agent B to the mixing tip 100, and to cause a mixer 130 to be rotated through connection of the mixing tip 100 to a drive unit, thus mixing the silicone base material A with the curing agent B. A person skilled in the art will appreciate that the dispenser 118 can be coupled to various parts of the mixing tip 100.

As illustrated in the drawings, the mixing tip 100 according to the present invention includes, in addition to the lower casing 110, an upper casing 120 coupled to an upper end of the lower casing 110 to discharge an impression material C to the outside. The mixer 130 which is also included in the mixing tip is disposed between the upper casing 120 and the lower casing 110 to mix the silicone base material A with the curing agent B.

Although not shown in the drawings, the lower casing 110 is coupled to a tip connection pipe (not shown) of an impression material cartridge mounted on the dispenser 118 to allow the silicone base material A and the curing agent B to be introduced into the lower casing 110.

The lower casing 110 includes a disk-shaped body 114, a ring-shaped upper casing-fitting ring 111 provided at an outer circumferential edge of the body 114, an inner fitting ring 112 disposed in the upper casing-fitting ring 111 with a predetermined spacing defined therebetween to support a coupling ring 127 of the upper casing 120, a base material supply pipe 113 and a curing agent supply pipe 115 extending downward from the body 114, into which the silicone base material A and the curing agent B are introduced, respectively, and a mixing shaft-fitting pipe 117 disposed between the base material supply pipe 113 and the curing agent supply pipe 115, in which a shaft-fitting pipe 133 of the mixer 130 is fitted.

As illustrated in FIG. 4, the body 114 is provided at a bottom surface thereof with a base material discharge hole 113a connected to the base material supply pipe 113 and a curing agent discharge hole 115a connected to the curing agent supply pipe 115. In this regard, the base material discharge hole 113a is sized such that the silicone base material A is introduced into the inside of a path control rib 137 of the mixer 130 disposed above the base material discharge hole 113a.

The curing agent discharge hole 115a is eccentrically positioned close to the inner fitting ring 112 such that the discharged curing agent B is not introduced into the inside of the path control rib 137 but is introduced into the mixing pipe 123 immediately after discharge thereof.

Furthermore, the inner fitting ring 112 is provided at an inner surface thereof with a curing agent guide groove 115c that is depressed by a predetermined depth and is connected to the curing agent discharge hole 115a. The curing agent guide groove 115c defines an outer path so as to prevent the curing agent B discharged from the curing agent discharge hole 115a from being introduced into the inside of the path control rib 137.

As illustrated in FIG. 5, the curing agent supply pipe 115 is provided with an inclined guide surface 115b to guide the curing agent B introduced from the dispenser (not shown) into the curing agent discharge hole 115a. Thanks to the provision of the inclined guide surface 115b, the curing agent B entering the curing agent supply pipe 115 may be introduced into the curing agent discharge hole 115a that is eccentrically positioned.

The upper casing 120 is coupled to an upper end of the lower casing 110. The upper casing 120 is spaced apart from the mixer 130 and defines therein a mixing space in which the silicone base material A and the curing agent B are mixed. The upper casing 120 includes an upper casing body 121 coupled to the lower casing 110, the mixing pipe 123 extending upward from the upper casing body 121, a discharge pipe 125 connected to the mixing pipe 123 to discharge the impression material C to the outside, and the coupling ring 127 fitted in the lower casing 110 and extending downward from the upper casing body 121.

The upper casing body 121 is configured to have the same diameter as the upper casing-fitting ring 111 and to be fitted around the outer surface of the upper casing-fitting ring 111, as illustrated in FIG. 5. In this regard, the coupling ring 127 extending downward from the upper casing body 121 is inserted between the upper casing-fitting ring 111 and the inner fitting ring 112 of the lower casing 110 by a predetermined depth and is screwed therewith for secure coupling therebetween.

The mixing pipe 123 is configured to have a pipe shape of a predetermined length so as to assure sufficient mixing efficiency of the silicone base material A with the curing agent B.

The mixing pipe 123 is configured to have an inner diameter corresponding to an outer diameter of mixing ribs 135*a* fixed to a mixing shaft 135. Consequently, the silicone base material A and the curing agent B are mixed with each other while passing between the rotating mixing ribs 135*a*, thus enhancing mixing efficiency.

The discharge pipe 125 is formed at a front end of the mixing pipe 123 to allow the impression material C which has been completely mixed to be discharged outward.

Meanwhile, the casing body 121 is provided at a lower surface thereof with a spacing protrusion 129 extending downward by a predetermined length. As illustrated in FIG. 5, the spacing protrusion 129 is configured to have a sufficient length to contact an upper surface of a mixing plate 131. Thanks to provision of the spacing protrusion, a clearance corresponding to the spacing protrusion 129 is defined between the mixing plate 131 and the casing body 121.

Therefore, the silicone base material A and the curing agent B, supply speeds of which are controlled in the space under the mixing plate 131, may be moved into the mixing pipe 123 through the clearance defined by the spacing protrusion 129.

The mixer 130 is disposed between the lower casing 110 and the upper casing 120 to mix the silicone base material A and the curing agent B, which have been introduced through the base material supply pipe 113 and the curing agent supply pipe 111, respectively. The mixer 130 is rotated between the lower casing 110 and the upper casing 120 by drive force transmitted from a mixing drive shaft (not shown) of the dispenser (not shown), thus mixing the silicone base material A with the curing agent B.

The mixer 130 includes the mixing plate 131 disposed in the inner fitting ring 112, the shaft-fitting pipe 133 extending downward from the mixing plate 131 and receiving driving force from the dispenser (not shown), the mixing shaft 135 vertically extending upward from the mixing plate 131, and the plurality of mixing ribs 135*a* radially extending from the mixing shaft 135 by a predetermined length.

The mixing plate 131 is configured to have a disk shape of a predetermined surface area. The mixing plate 131 prevents the silicone base material A introduced in the base material supply pipe 113 from being directly introduced into the mixing pipe 123. The silicone base material A is charged in a space under the mixing plate 131 by a predetermined amount while contacting the mixing plate 131, and then is introduced into the mixing pipe 123.

The shaft-fitting pipe 133 is fitted in the mixing shaft-fitting pipe 117 and extends downward therefrom. The shaft-fitting pipe 133 is fitted around the drive shaft (not shown) of the dispenser (not shown) to receive the driving force. As the shaft-fitting pipe 133 rotates, the entire mixer 130 is rotated in the upper casing 120, thus mixing the silicone base material A with the curing agent B.

The mixing shaft 135 coaxially extends from the shaft-fitting pipe 133 by a predetermined length. The mixing shaft 135 supports the plurality of mixing ribs 135*a*. The plurality of mixing ribs 135*a* radially extend from the mixing shaft 135 while being uniformly spaced from one another by a predetermined angle. In a preferred embodiment of the present invention, the plurality of mixing ribs 135*a* are horizontally disposed to be uniformly spaced from one another by a right angle and are longitudinally disposed along the mixing shaft 135 to be uniformly spaced from one another.

In some cases, the plurality of mixing ribs 135*a* may be axially disposed while being spaced from one another by different angles, or may be alternately disposed in the axial direction.

The path control rib 137 extends downward from the outer circumferential edge of the mixing plate 131 by a predetermined length. The path control rib 137 defines a stagnant space under the mixing plate 131 such that paths through which the silicone base material A and the curing agent B are initially discharged differ from each other and, as such, the silicone base material A initially discharged resides in the path control rib 137. Consequently, the path control rib 137 functions to cause the curing agent B to be first introduced into the curing agent guide groove 115*c* before introduction of the silicone base material A.

As illustrated in FIG. 5, the path control rib 137 is formed at a position corresponding to a diameter of the base material-discharge hole 113*a*. Therefore, the silicone base material A is discharged from the base material-discharge hole 113*a* and then is introduced into the buffer space defined by the path control rib 137 and a lower surface of the mixing plate 131.

When the silicone base material A is continuously introduced and thus the buffer space is filled with the silicone base material A, the silicone base material A is extruded through a clearance defined between the path control rib 137 and the bottom surface of the body 114 and then is introduced into the mixing pipe 123 due to the pressure of the silicone base material A which is continuously charged.

Meanwhile, since there is no interference between the path control rib 137 and the curing agent-discharge hole 115*a*, the curing agent B which has been discharged through the curing agent-discharge hole 115*a* is not introduced into the mixing space in the path control rib 137 but is introduced into the mixing pipe 123 through the curing agent guide groove 115*c*.

In other words, the path control rib 137 functions to supply the silicone base material A and the curing agent B to be supplied into the mixing pipe 123 through different flow paths. Consequently, the silicone base material A is transferred into the mixing pipe 123 through a longer flow path than a flow path of the curing agent B.

An operation of discharging the impression material C through the mixing tip 100 according to the present invention which is configured in the above-described manner will be described with reference to FIGS. 2 to 5.

Upon activation of the dispenser, the silicone base material A and the curing agent B are introduced into the lower casing 110. The silicone base material A is then supplied into the base material supply pipe 113 while the curing agent B is supplied into the curing agent supply pipe 115.

The silicone base material A which has been introduced through the base material supply pipe 113 is introduced into the buffer space defined between the path control rib 137 and the mixing plate 131 through the base material discharge hole 113*a* and resides therein for a period of time required to fully fill the buffer space with the silicone base material A. The silicone base material A is extruded and transferred to the mixing pipe 123 under the pressure of the silicone base material A which is continuously accumulated.

Meanwhile, the curing agent B which has been introduced through the curing agent supply pipe 115 flows into the curing agent discharge hole 115a by guidance of the inclined guide surface 115b, and immediately flows into the mixing pipe 123 through the curing agent guide groove 115c.

In a mixing procedure, when supply pressures applied from the dispenser (not shown) for the silicone base material A and the curing agent B are the same, the silicone base material A is supplied into the base material pipe 113 and the curing agent B is concurrently supplied into the curing agent supply pipe 115. In this case, there is a difference between a supply amount of the silicone base material A and a supplied amount of the curing agent B and, as such, an impression material that is abnormally mixed may be formed.

The difference between both supply amounts is compensated by the silicone base material A residing in the buffer space defined between the path control rib 137 and the mixing plate 131.

Accordingly, by first introducing the curing agent and then introducing the silicone base material into the mixing pipe 131, even an impression material C that is initially discharged may have a desired mixing ratio.

Therefore, a user can instantly use the entire impression material without the need to discard the portion of the impression material that is initially discharged.

In this regard, the amount of the silicone base material A residing in the buffer space may be controlled through proper adjustment of the diameter of the base material discharge hole 113, the diameter of the curing agent discharge hole 115a, the volume of the buffer space defined between the path control rib 137 and the mixing plate 131, the distance between the path control rib 137 and the body 114, and so forth.

Figure 6:
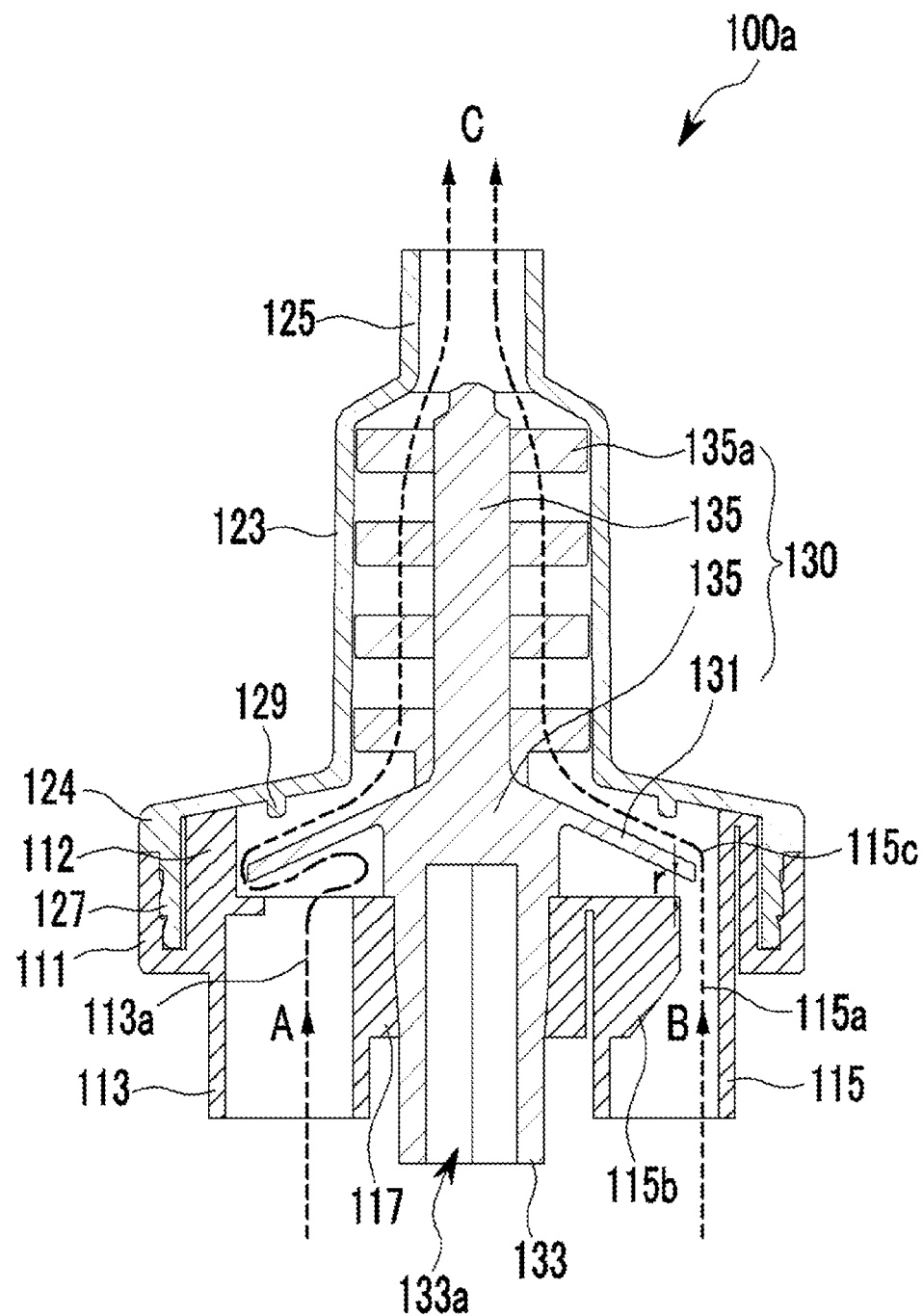
FIGS. 6 and 7 are cross-sectional views showing mixing tips according to other embodiments of the present invention.

FIG. 6 is a schematic view illustrating a construction of a mixing tip 100a according to another embodiment of the present invention.

In comparison of FIG. 6 with FIG. 5, the mixing tip 100a according to another embodiment of the present invention is configured such that only the mixing plate 131 is provided without the path control rib 137. Furthermore, the outer circumferential edge of the mixing plate 131 is more steeply inclined with respect to the center region. Consequently, a spacing "r" between the mixing plate 131 and the base material discharge hole 113a is reduced, so that the curing agent B flows without introduction into the buffer space.

The mixing tip 100 according to the previous preferred embodiment of the present invention is configured such that the path control rib 137 physically precludes flow of the silicone base material A and, as such, the period of time for which the silicone base material A resides in the buffer space is increased. Meanwhile, the curing agent B is immediately supplied into the mixing pipe 123 through the curing agent guide groove 115c and resides therein. As a result, a proportion of the curing agent B that is introduced into the mixing pipe 123 is excessively increased, and thus there is a risk that the mixed impression material C is overly quickly cured.

In contrast, the mixing tip 100a according to another embodiment of the present invention is configured to prevent a cured portion of the silicone base material A initially discharged from being introduced into the mixing pipe 123 and to reduce an amount of the silicone base material A that resides in the buffer space by absence of the path control rib 137. Therefore, speed of mixing and reaction of the silicone base material A and the curing agent B in the mixing pipe 123 may be controlled by adjusting an amount of the silicone base material A that resides in the buffer space.

Figure 7:
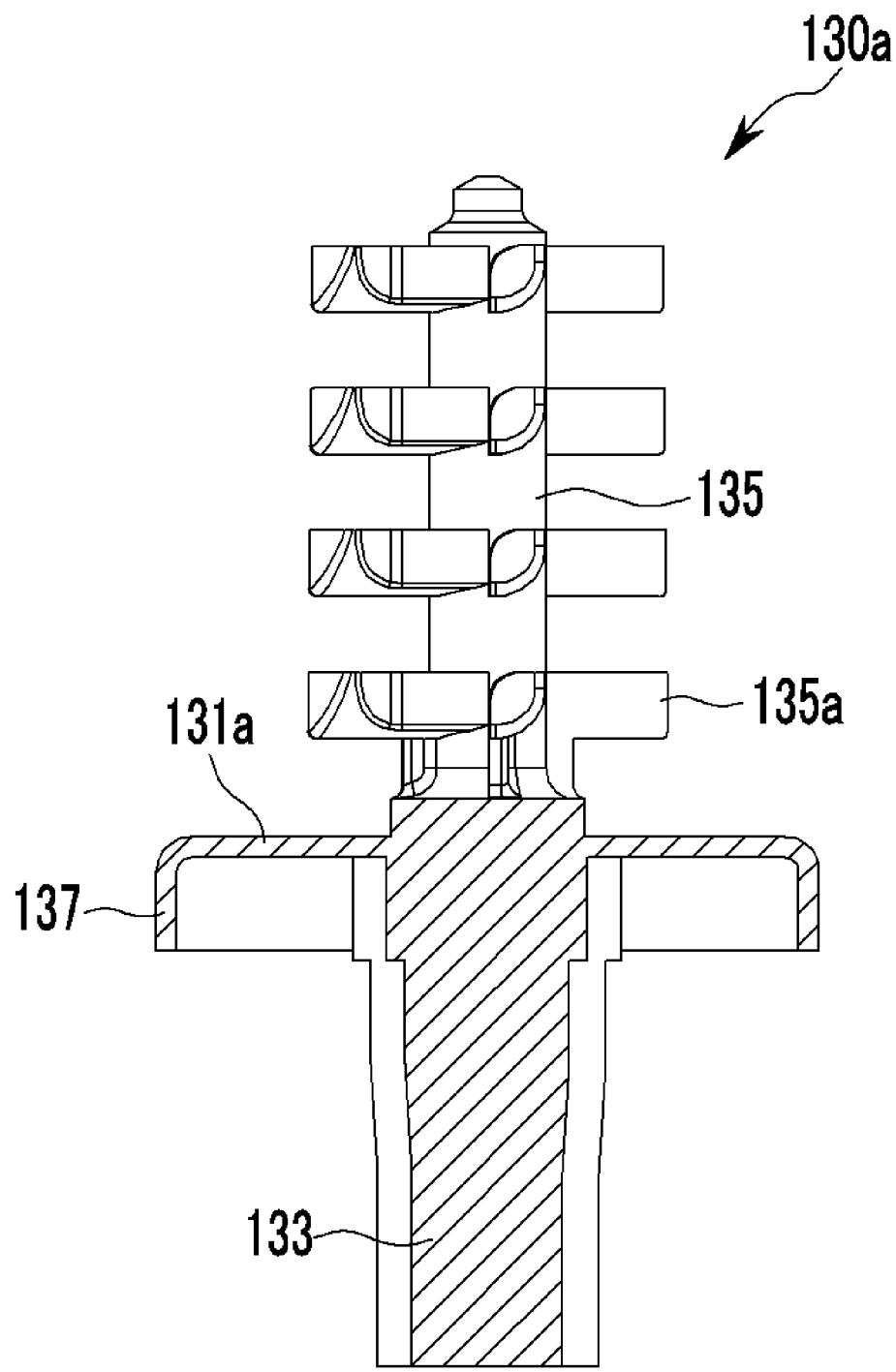

As illustrated in FIG. 7, a mixing tip 100b may include a mixing plate 131a which is horizontally formed. In this case, since the mixing plate 131a is provided at a peripheral edge thereof with a path control rib 137, a portion of the silicone base material A that is initially cured and discharged is inevitably accommodated in the buffer space. Therefore, even though the mixing plate 131a is horizontally constructed, the mixing plate 131a may function appropriately.

In some cases, the mixing tip 100 may be configured without the spacing protrusion 129. This is because displacements of the mixing shaft 135 and the mixing ribs 135a are restricted in that the diameter of the discharge pipe 125 is reduced relative to the mixing pipe 123 even though there is no spacing protrusion 129.

As described above, the mixing tip according to the present invention can eliminate the difference in supply time between a silicone base material and a curing agent which are initially discharged by adjusting supply paths of the silicone base material and the curing agent.

Consequently, even a portion of an impression material that is initially discharged may be formed to have a desired mixing ratio, and thus it is possible to eliminate the conventional trouble that an initially discharged portion of an impression material has to be discarded.

A mixing tip of the present invention has been described merely for illustrative purposes, and those skilled in the art will appreciate that various modifications and equivalent embodiments are possible. Therefore, it will be understood that the present invention is not limited to the embodiments described above. The true technical protective scope of the invention should be defined by the appended claims. Furthermore, it should also be understood that the present invention embraces all modifications and equivalents that fall within the spirit and scope defined in the appended claims.

The invention claimed is:

1. A mixing tip for a dispenser, comprising:
a lower casing configured to be connected to the dispenser and to receive a silicone base material and a curing agent;
an upper casing coupled to the lower casing and including a discharge pipe through which an impression material having a desired mixing ratio of the silicone base material and the curing agent is discharged to the outside; and
a mixer disposed between the lower casing and the upper casing to mix the silicone base material with the curing agent,
wherein the mixer comprises:
a mixing plate disposed between the lower casing and the upper casing and having a predetermined surface area;
a shaft-fitting pipe extending downward from the mixing plate and configured to be fitted over a drive shaft of the dispenser to be rotated therewith; and
a path control rib extending downward from an outer peripheral edge of the mixing plate to control flow paths of the silicone base material and the curing agent; and
wherein the lower casing comprises:
a body comprising an upper casing-fitting ring formed at an outer peripheral edge thereof and coupled to the upper casing and an inner fitting ring spaced apart from the upper casing-fitting ring by a predetermined interval and extending from the body;
a base material supply pipe extending downward from a bottom surface of the body to receive the silicone base material and to discharge the silicone base material into a buffer space defined between the path control rib and the mixing plate; and
a curing agent supply pipe spaced apart from the base material supply pipe to receive the curing agent and to discharge the curing agent into a space defined between the path control rib and the inner fitting ring so as to guide the curing agent to bypass the buffer space.

2. The mixing tip for a dispenser according to claim 1, wherein the curing agent supply pipe has at an inner surface thereof an inclined guide surface for guiding the curing agent introduced from the dispenser toward the inner fitting ring.

3. The mixing tip for a dispenser according to claim 2, wherein the inner fitting ring has at an inner surface thereof a curing agent guide groove having a predetermined depth, the curing agent guide groove being connected to an upper end of the curing agent supply pipe to guide the curing agent toward the outside of the path control rib.

4. The mixing tip for a dispenser according to claim 1, further including a mixing pipe disposed between the mixing plate and the discharge pipe, the mixing pipe being in fluid communication with the discharge pipe.

5. The mixing tip for a dispenser according to claim 4, wherein the path control rib is configured to guide the curing agent directly into the mixing pipe, and wherein the buffer space is configured to accumulate the silicone base material before the silicone base material is introduced into the mixing pipe.

6. The mixing tip for a dispenser according to claim 4, the path control rib is configured to guide the curing agent and the silicone base material towards the mixing pipe through separate flow paths.

7. A mixing tip for a dispenser, comprising:
a lower casing configured to be connected to the dispenser and to receive a silicone base material and a curing agent;
an upper casing coupled to the lower casing and including a discharge pipe through which an impression material having a desired mixing ratio of the silicone base material and the curing agent is discharged to the outside; and
a mixer disposed between the lower casing and the upper casing to mix the silicone base material with the curing agent,
wherein the mixer comprises:
a mixing plate disposed between the lower casing and the upper casing and having a predetermined surface area; and
a shaft-fitting pipe extending downward from the mixing plate and configured to be fitted over a drive shaft of the dispenser to be rotated therewith, and
wherein the lower casing comprises:
a body comprising an upper casing-fitting ring formed at an outer peripheral edge thereof and coupled to the upper casing and an inner fitting ring spaced apart from the upper casing-fitting ring by a predetermined interval and extending from the body;
a base material supply pipe extending downward from a bottom surface of the body to receive the silicone base material and to discharge the silicone base material into a buffer space under the mixing plate; and
a curing agent supply pipe spaced from the base material supply pipe to receive the curing agent and to discharge the curing agent along the inner fitting ring without introducing the curing agent into the buffer space.

8. The mixing tip for a dispenser according to claim 7, further including a mixing pipe disposed between the mixing plate and the discharge pipe, the mixing pipe being in fluid communication with the discharge pipe.

9. The mixing tip for a dispenser according to claim 8, wherein the mixing plate is configured to guide the curing agent directly into the mixing pipe.

* * * * *